United States Patent
Eshoo et al.

(10) Patent No.: US 9,914,965 B2
(45) Date of Patent: Mar. 13, 2018

(54) RAPID WHOLE GENOME AMPLIFICATION

(71) Applicant: Ibis Biosciences, Inc., Carlsbad, CA (US)

(72) Inventors: Mark Eshoo, Solana Beach, CA (US); Stanley Motley, Carlsbad, CA (US); John Picuri, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 15/250,259

(22) Filed: Aug. 29, 2016

(65) Prior Publication Data

US 2017/0067089 A1    Mar. 9, 2017

Related U.S. Application Data

(63) Continuation of application No. 13/339,633, filed on Dec. 29, 2011, now Pat. No. 9,428,801.

(60) Provisional application No. 61/428,076, filed on Dec. 29, 2010.

(51) Int. Cl.
   *C12P 19/34*    (2006.01)
   *C12Q 1/68*     (2018.01)

(52) U.S. Cl.
   CPC ............. *C12Q 1/686* (2013.01); *C12P 19/34* (2013.01); *C12Q 1/6846* (2013.01)

(58) Field of Classification Search
   CPC ............. C12Q 1/686; C12Q 2521/525; C12Q 2525/179; C12Q 2527/125; C12Q 1/6846; C12P 19/34
   USPC ........................................................ 435/91.2
   See application file for complete search history.

(56) References Cited

U.S. PATENT DOCUMENTS

2011/0224105 A1*  9/2011  Kurn .................. C12P 19/34
                                                        506/26

FOREIGN PATENT DOCUMENTS

WO    WO 2008151023    * 12/2008

* cited by examiner

*Primary Examiner* — Cynthia B Wilder
(74) *Attorney, Agent, or Firm* — Casimir Jones, S.C.

(57) ABSTRACT

The present invention provides compositions and methods for rapidly amplifying target nucleic acid (e.g., using whole genome amplification) that allows small amounts of starting nucleic acid to be employed. In certain embodiments, the methods employ compositions that comprise: phi29 polymerase, exo– Klenow polymerase and/or Klenow polymerase, dNTPs, primers, and a buffering agent. In some embodiments, the target nucleic acid is amplified at a rate that would result in at least 1000-fold amplification in thirty minutes.

18 Claims, 10 Drawing Sheets

RAPID WHOLE GENOME AMPLIFICATION

The present Application is a continuation of U.S. application Ser. No. 13/339,633 filed Dec. 29, 2011, which claims priority to U.S. Provisional Application Ser. No. 61/428,076 filed Dec. 29, 2010, the entirety of each of which is herein incorporated by reference.

FIELD OF THE INVENTION

The present invention provides compositions and methods for rapidly amplifying target nucleic acid (e.g., using whole genome amplification) that allows small amounts of starting nucleic acid to be employed. In certain embodiments, the methods employ compositions that comprise: phi29 polymerase, exo– Klenow polymerase and/or Klenow polymerase, dNTPs, primers, and a buffering agent. In some embodiments, the target nucleic acid is amplified at a rate that would result in at least 1000-fold amplification in thirty minutes.

BACKGROUND

In many fields of research such as genetic diagnosis, cancer research or forensic medicine, the scarcity of genomic DNA can be a severely limiting factor on the type and quantity of genetic tests that can be performed on a sample. One approach designed to overcome this problem is whole genome amplification. The objective is to amplify a limited DNA sample in a non-specific manner in order to generate a new sample that is indistinguishable from the original but with a higher DNA concentration. The aim of a typical whole genome amplification technique is to amplify a sample up to a microgram level while respecting the original sequence representation.

The first whole genome amplification methods were described in 1992, and were based on the principles of the polymerase chain reaction. Zhang and coworkers (Zhang, L., et al. Proc. Natl. Acad. Sci. USA, 1992, 89: 5847-5851; herein incorporated by reference) developed the primer extension PCR technique (PEP) and Telenius and collaborators (Telenius et al., Genomics. 1992, 13(3):718-25; herein incorporated by reference) designed the degenerate oligonucleotide-primed PCR method (DOP-PCR). PEP involves a high number of PCR cycles, generally using Taq polymerase and 15 base random primers that anneal at a low stringency temperature. DOP-PCR is a method which generally uses Taq polymerase and semi-degenerate oligonucleotides (such as CGACTCGAGNNNNNNATGTGG (SEQ ID NO: 1), for example, where N=A, T, C or G) that bind at a low annealing temperature at approximately one million sites within the human genome. The first cycles are followed by a large number of cycles with a higher annealing temperature, allowing only for the amplification of the fragments that were tagged in the first step.

Multiple displacement amplification (MDA, also known as strand displacement amplification; SDA) is a non-PCR-based isothermal method based on the annealing of random hexamers to denatured DNA, followed by strand-displacement synthesis at constant temperature (Blanco et al., 1989, J. Biol. Chem. 264:8935-40; Dean, F. B. et al. (2002) Comprehensive human genome amplification using multiple displacement amplification; Proc. Natl. Acad. Sci. USA 99, 5261; and Van, J. et al. (2004) Assessment of multiple displacement amplification in molecular epidemiology. Biotechniques 37, 136; all of which are herein incorporated by reference). It has been applied to small genomic DNA samples, leading to the synthesis of high molecular weight DNA with limited sequence representation bias (Lizardi et al., Nature Genetics 1998, 19, 225-232; Dean et al., Proc. Natl. Acad. Sci. U.S.A. 2002, 99, 5261-5266; both of which are herein incorporated by reference). As DNA is synthesized by strand displacement, a gradually increasing number of priming events occur, forming a network of hyperbranched DNA structures. The reaction can be catalyzed by the Phi29 DNA polymerase or by the large fragment of the Bst DNA polymerase. The Phi29 DNA polymerase possesses a proofreading activity resulting in error rates 100 times lower than the Taq polymerase. MDA type methods, however, require many hours (e.g., 6 hours) to generate a sufficient fold amplification.

What is needed are whole genome amplification methods that are faster than known methods.

SUMMARY OF THE INVENTION

The present invention provides compositions and methods for rapidly amplifying target nucleic acid (e.g., using whole genome amplification) that allows small amounts of starting nucleic acid to be employed. In certain embodiments, the methods employ compositions that comprise: phi29 polymerase (or Bst DNA polymerase, or other strand displacing polymerase), exo– Klenow polymerase and/or Klenow polymerase (or other DNA polymerase), dNTPs, primers, and a buffering agent. In some embodiments, the target nucleic acid is amplified at a rate that would result in at least 1000-fold amplification in thirty minutes.

In some embodiments, the present invention provides methods of amplifying target nucleic acid comprising: a) providing a sample comprising: i) target nucleic acid, ii) phi29 polymerase (or Bst DNA polymerase, or other strand displacing polymerase), iii) exo– Klenow polymerase and/or Klenow polymerase (or other DNA polymerase), iv) dNTPs, v) primers, and vi) a buffering agent; and b) treating the sample under conditions such that the target nucleic acid is amplified thereby generating amplified target nucleic acid. In certain embodiments, the treating is conducted for no more than 4 hours (e.g., no more than 2 hours . . . no more than 1.5 hours . . . no more than 1.0 hour . . . no more than 45 minutes . . . no more than 35 minutes . . . no more than 30 minutes . . . no more than 15 minutes). In certain embodiments, the treating is conducted between 10 minutes and 2 hours (e.g., 15 minutes-1.5 hours or 20 minutes to 1 hour).

In certain embodiments, the present invention provides compositions or samples comprising: i) phi29 polymerase (or Bst DNA polymerase, or other polymerase, such as a strand displacing polymerase), ii) exo– Klenow polymerase and/or Klenow polymerase (or other DNA polymerase), iii) dNTPs, iv) primers, and iv) a buffering agent. In particular embodiments, the compositions or samples further comprise target nucleic acid.

In particular embodiments, the treating is under isothermal conditions. In other embodiments, the target nucleic acid is amplified at a rate that would result in at least 200-fold . . . 500-fold . . . 1000-fold . . . 1500-fold . . . 2000-fold . . . or at least 2500-fold amplification in 30 minutes. In certain embodiments, the target nucleic acid is present in the sample (or composition) at a level between 1 ng and 100 ng (e.g., 1-10 ng; 10-40 ng; 50-75 ng; 75-100 ng).

In other embodiments, the primers are random primers. In certain embodiments, the target nucleic acid is genomic DNA. In some embodiments, the sample further comprises a phosphatase. In particular embodiments, the sample further comprises a pyrophosphatase. In additional embodiments, the dNTPs are at a concentration of at least 10 mM of each of the four bases (e.g., at least 10 mM . . . at least 15 mM . . . at least 20 mM . . . at least 25 mM . . . at least 30 mM or higher).

In some embodiments, the sample comprises the Klenow polymerase. In further embodiments, the sample comprises the exo– Klenow polymerase. In additional embodiments, the buffering agent comprises tris(hydroxymethyl) aminomethane (TRIS).

In particular embodiments, the sample (or composition) further comprises at least one component (or at least two, or at least three, or at least four, or all five components) selected from the group consisting of: an emulsifier, a divalent metal cation, an inorganic salt, an alpha-linked disaccharide, and a reducing agent. In other embodiments, the emulsifier is a polysorbate. In some embodiments, the polysorbate is selected from the group consisting of: Tween 20, Tween 40, Tween 60, or Tween 80. In other embodiments, the inorganic salt is ammonium sulfate. In additional embodiments, the alpha-linked disaccharide comprises Trehalose. In some embodiments, the reducing agent comprises dithiothreitol (DTT).

DETAILED DESCRIPTION

Figure 1:
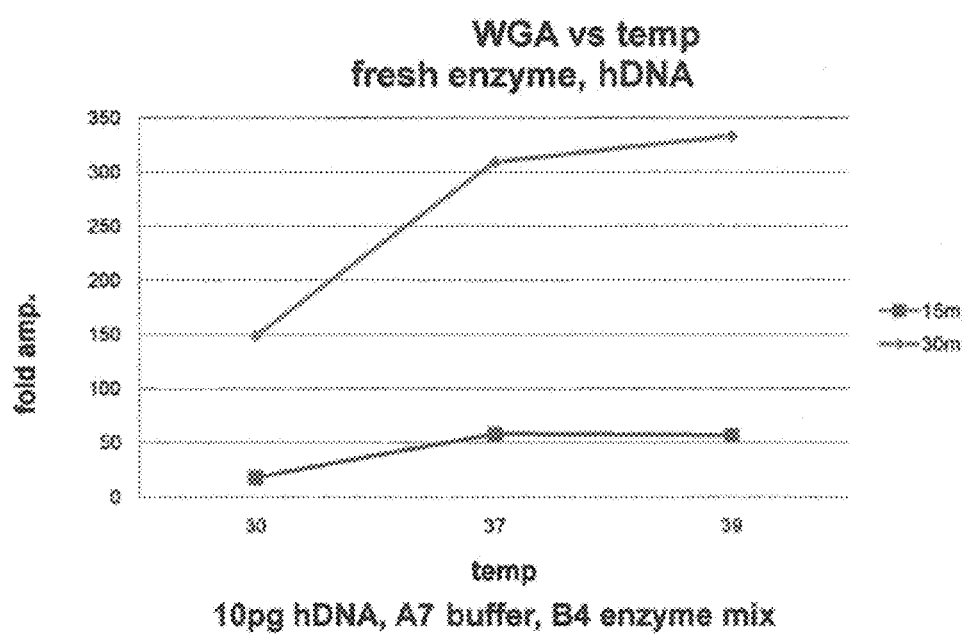
FIG. 1 shows fold-amplification WGA results from Example 1 where the A7 buffer and B4 enzyme were tested at various times (15 minutes and 30 minutes) and various temperatures (30 C, 37 C, and 39 C).
Figure 2:
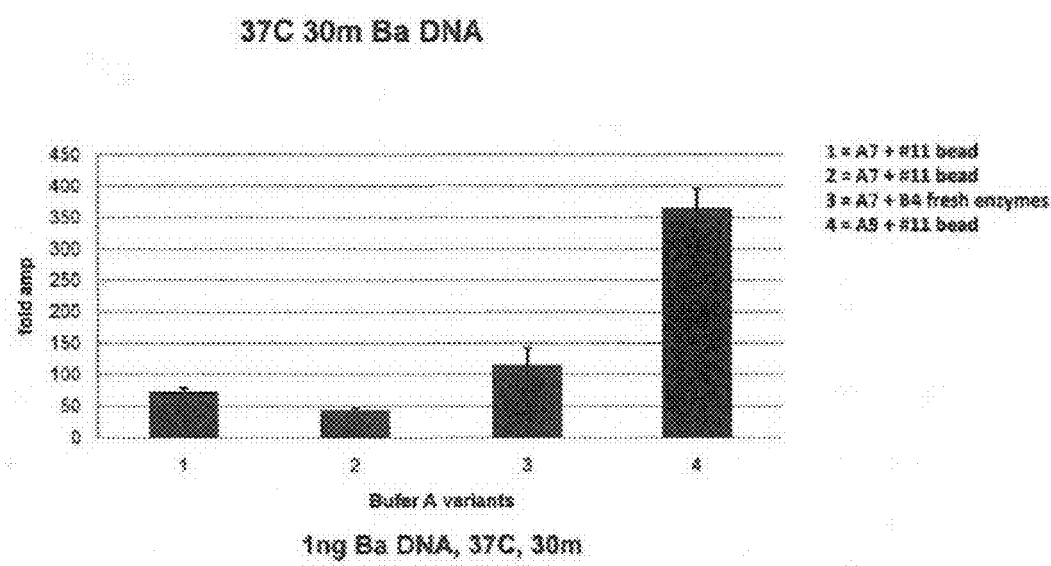
FIG. 2 shows a comparison of the fold-amplification results using the A7 and A9 buffers in whole genome amplification at 37 C for 30 minutes.

The present invention provides compositions and methods for rapidly amplifying target nucleic acid (e.g., using whole genome amplification) that allows small amounts of starting nucleic acid to be employed. In certain embodiments, the methods employ compositions that comprise: phi29 polymerase, exo– Klenow polymerase and/or Klenow polymerase, dNTPs, primers, and a buffering agent. In some embodiments, the target nucleic acid is amplified at a rate that would result in at least 1000-fold amplification in thirty minutes.

The present invention provides methods for the rapid amplification of whole genomic DNA. In certain embodiments, the methods of the present invention are able to generate significant amounts of DNA from trace levels. This allows samples with very low levels of DNA content to be amplified and used, for example, in further diagnostic tests (e.g., forensic testing). For example, the reaction conditions provided by embodiments of the present invention generate 2-5 ug of DNA from 1 ng of starting DNA (~2500× amplification), in a 30 minute reaction.

In the prior art, whole genome amplification reactions took many hours (e.g., 6-12 hours) to generate a significant amount of material. The present invention greatly shortens this time requirement (e.g., reduces the time to 30 minutes).

In certain embodiments, the buffer and enzyme mixture shown in Table 1, or similar mixtures are employed.

TABLE 1

| Template DNA | |
|---|---|
| Tris HCL | 0.04025 M |
| Tris Base | 0.00975 M |
| MgCl2 | 0.012 M |
| $(NH_4)_2SO_4$ | 0.01 M |
| Trehalose | 0.5656 M |
| Tween-40 | 1 % |
| DNTP mix 100 mM (25 mM each) Bioline | 2.8 mM |
| DTT | 0.004 M |
| Primer Mix | 0.05 mM |
| Enzyme mix 1 ul = 50U Phi29 & 20U Klenow & 009U | 100 ul |
| Pyrophosphatase | 2 ul rxn |

One exemplary protocol using the mixture from Table 1 is as follows. The starting genomic DNA (>10 pg-1 ng) is added to the buffer mixture in Table 1 to a final volume of 96 ul. The DNA is heat denatured at 95 C for 1 minute, and the cooled to 4 C and held at that temperature for 30 minutes (for amplification). Then mixture is then incubated at 75 C for 10 minutes for heat inactivation of the enzymes. The levels of amplification may be determined qualitatively by gel electrophoresis and quantitatively by qPCR reactions.

The present invention shortens the time and increases the yield of current whole genome amplification protocols. Therefore, in some embodiments, it is useful in any assay that requires large amounts of DNA or assays that require a trace sample to be split into many test reactions such as Next Gen Sequencing Sanger sequencing, DNA microarrays, Broad-range PCR.

EXAMPLES

Materials and Methods for the Examples Below

The buffer and enzyme formulations that were employed are shown in Table 2 below:

TABLE 2

| Buffer Formulations | | | |
|---|---|---|---|
| | A7 base | Pellet A-Mix | A9 base |
| Tris pH 7.6 | 50 mM | 50 mM | 50 mM |
| MgCl2 | 12 mM | 12 mM | 12 mM |

TABLE 2-continued

Buffer Formulations

| | A7 base | Pellet A-Mix | A9 base |
|---|---|---|---|
| (NH4)2SO4 | 10 mM | 10 mM | 10 mM |
| Betaine | 566 mM | 0 mM | 0 mM |
| Trehalose | 566 mM | 566 mM | 566 mM |
| Tween 40 | 1% (w/v) | 0.05% (w/v) | 1% (w/v) |
| DTT | 0 mM | 4 mM | 0 mM |

It is noted that making complete A7 buffer or A9 buffer involves adding primers, dNTPs and DTT as described in the Examples below.
Pellet A-mix already has primers and DNTPs at the concentrations found in A7
The additional enzyme mixes and enzyme pellets employed are shown in Table 3 below.

TABLE 3

| | B4 | Enzyme Pellets (ie #11, B4, etc.) |
|---|---|---|
| Phi 29 Polymerase | 44.8 units | 44.8 units |
| Pyrophospatase | 0.007 units | 0.007 units |
| Polymerase Pol I | 0.90 units | 0.90 units |
| BSA | 37.5 ug | 37.5 ug |
| Glycerol | 50% (v/v) | 0% (v/v) |

It is noted that all of the lyophilized enzymes used are the same formulation despite different names.

| A-mix for pellets | |
|---|---|
| | Per 100 ul Rxn |
| A mix | 47.80 |
| DTT | 0.38 |
| Primer | 4.77 |
| DNTP | 1.91 |
| Poly A | 0.14 |
| total | 55.00 |
| water | 15.00 |

| A-mix fix for pellets | |
|---|---|
| | Per 100 ul Rxn |
| A mix | 53.13 |
| DTT | 0.38 |
| Primer | 4.77 |
| DNTP | 1.91 |
| Poly A | 0.14 |
| total | 60.33 |
| water | 9.68 |

Example 1

Selection of Time and Temperature for Whole Genome Amplification Reactions

In this Example, varying temperature (30, 37 and 39 C) were tested for 15 and 30 minutes with whole genome amplification methods. Each reaction has 100 ul total volume in A7 complete with 1 ng human genomic DNA. The reactions were heated to 95 C for 1 minute and then cooled to 0 C and held at that temperature for 5 minutes. Then, 5 ul of B4 whole genome amplification (WGA) enzymes were added, the reactions were mixed with vortexing and held at 4 C for 10 m, followed by shifting the reactions to either 30 C, 37 C or 39 C for either 15 or 30 minutes. The reactions were heat killed at 65 C for 10 minutes followed by holding the reactions at 4 C till needed. The results are shown in FIG. 1, which showed that 30 minutes at 37 C gave good fold amplification.

It is noted, to make A7 complete, 1000 ul of A7 base (see Table 2) was combined with 6.1 ul 1M DTT, 75.9 ul of 1 mM random 7mers, 30.4 ul of dNTP (25 mM each) and 2.3 ul of polyA (1 mg/ml sonicated). For quantitating the results (shown in FIG. 1), 2 ul of each reaction was diluted in 18 ul of DNA dilution buffer, sonicated in a water bath sonicator >200 W for 3 minutes at 4 C. The samples were then tested in qPCR reaction with a standard curve of human genomic DNA.

Example 2

Whole Genome Amplification Buffer Optimizations

This Example performed whole genome amplification at 37 C for 30 minutes with different buffer formations. All reactions were at 100 ul total volume in thin walled PCR tubes with 1 ng of *B. anthracis* (BA) DNA. The buffer in reaction 1 was "Amix for pellets" buffer. Reaction 2 buffer was "Amix-fix for pellets," reaction 3 buffer was A7 complete, and reaction buffer #4 was A9-pellets+$H_2O$.

All reactions were heated to 95 C for 2 minutes, then cooled to 4 C for 5 minutes. To reactions 1, 2 and 4 there was 1 WGA enzyme pellet #11 added. B4 enzyme mix (5 ul) was added to reaction 3. All reactions were vortexed, heated to 37 C for 30 minutes, followed by 65 C for 10 m and shifted to 4 C to hold. No template controls were included with no BA DNA. Each test condition was tested in duplicate. Fold amplification was determined with BA specific qPCR reactions. The results are shown in FIG. 2, which show that the A9 buffer, using 37 C for 30 minutes, provided increased fold amplification.

Example 3

WGA Enzyme Optimization

This Example explored the effects of additions of *E. coli* DNA polymerase, Klenow exo− enzyme, and T4 DNA polymerase to the WGA reactions with and without the addition of higher levels of dNTP.

A9 complete buffer was made with the following reagents:

| | | |
|---|---|---|
| A9 base | bag5 | 1000 |
| DTT | 1M | 6.5 |
| Primers | 1 mM | 81.2 |
| dNTP | 25 mM each (C13) | 32.5 |
| dH20 | | 16.2 |
| | | 1136.4 total volume. |

All reactions were at 100 ul total volume in A9 complete buffer in thin walled PCR tubes with 200 pg of *K. pneumoniae* (KP) DNA. Each reaction was heated to 95 C for 1 m and cooled to 4 C for 5 m. Then the following additions were made:

To reaction 1, 1 WGA enzyme bead #11.

To reaction 2, 1 WGA enzyme bead #11 and 40 u of Klenow exo-.

To reaction 3, 1 WGA enzyme bead #11, 40 u of Klenow exo- and 4 ul dNTP mix (10 mM each).

To reaction 4, 1 WGA enzyme bead #11 and 6 u of T4 DNA polymerase.

To reaction 5, 1 WGA enzyme bead #11 and 18 u of T4 DNA polymerase.

To reaction 6, 5 ul of B4 enzyme mix.

To reaction 7, 5 ul of B4 enzyme mix and 40 u of Klenow exo-.

To reaction 8, 5 ul of B4 enzyme mix and 40 u of Klenow exo- and 4 ul of dNTP.

Figure 3:
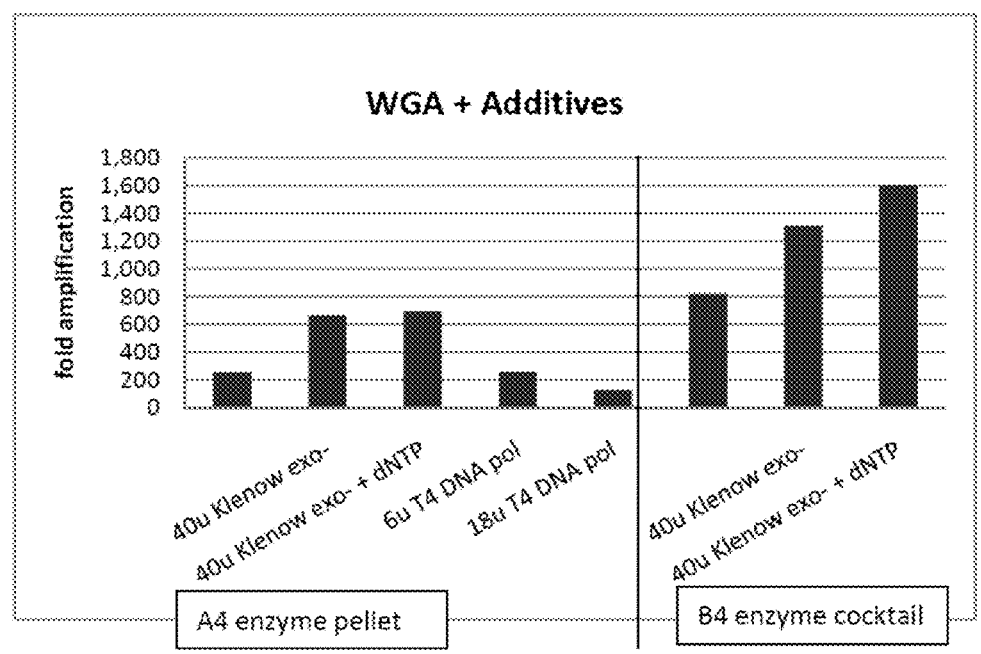
FIG. 3 shows fold-amplification WGA results from Example 3 where various enzymes were tested.

All reactions were brought to 100 ul with $H_2O$. Each reaction was vortexed well and incubated at 37 C for 30 m, followed by a 75 C 10 m incubation and then the reactions were stored at -20 C. The DNA amplification was quantitated with a K. pneumoniae specific qPCR reaction. Results are shown in FIG. 3, which shows that additional Klenow exo- and dNTPs enhances the speed of WGA, while T4 DNA polymerase decreases the speed of WGA.

Example 4

Addition of Other DNA Polymerases to WGA Reaction

This Example was used to determine the effects of the addition of other DNA polymerases to the WGA reaction. Each reaction was run in A9 complete with 1 ng of K. pneumoniae genomic DNA. Each reaction contained 70 ul and was heated to 95 C for 1 m followed by 15 minutes at 4 C.

To reaction 1 was added 50 u of Phi29 DNA polymerase.

To reaction 2 was added 50 u of Phi29 DNA polymerase and 5 u of E. coli DNA polymerase.

To reaction 3 was added 50 u of Phi29 DNA polymerase, 5 u of E. coli DNA polymerase and 40 u of Klenow exo-.

To reaction 4 was added 5 u of E. coli DNA polymerase and 40 u of Klenow exo-.

To reaction 5 was added 40 u of Klenow exo-.

Figure 4:
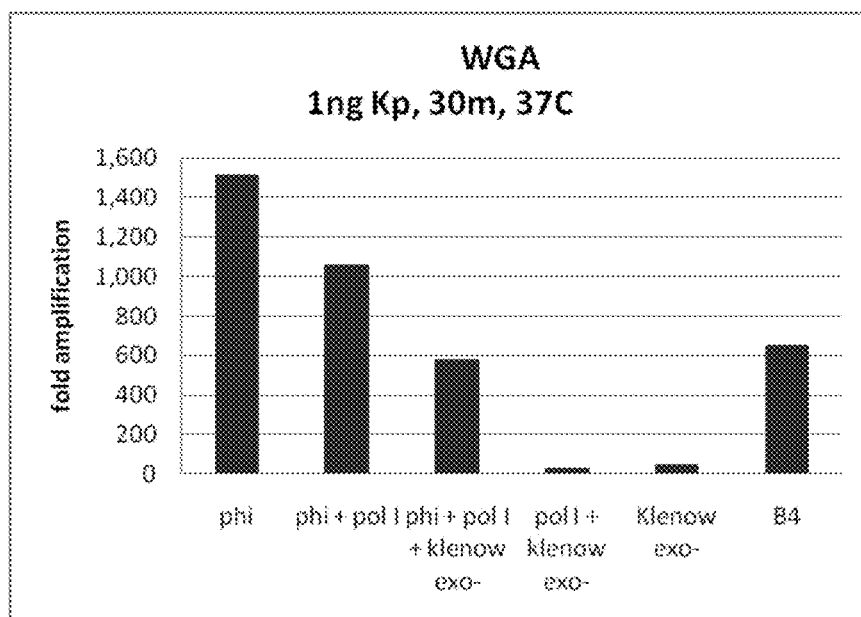
FIG. 4 shows fold-amplification WGA results from Example 4 where various enzyme and enzyme combinations were tested.

To reaction 6 was added 5 ul of B4 WGA enzyme mix. Each reaction was incubated at 37 C for 30 m followed by a heat inactivation at 75 C for 10 m. Reactions were stored at -20 C. The results are shown in FIG. 4.

Example 5

Optimizing WGA Reaction Components in A9 Complete Buffer

Figure 5:
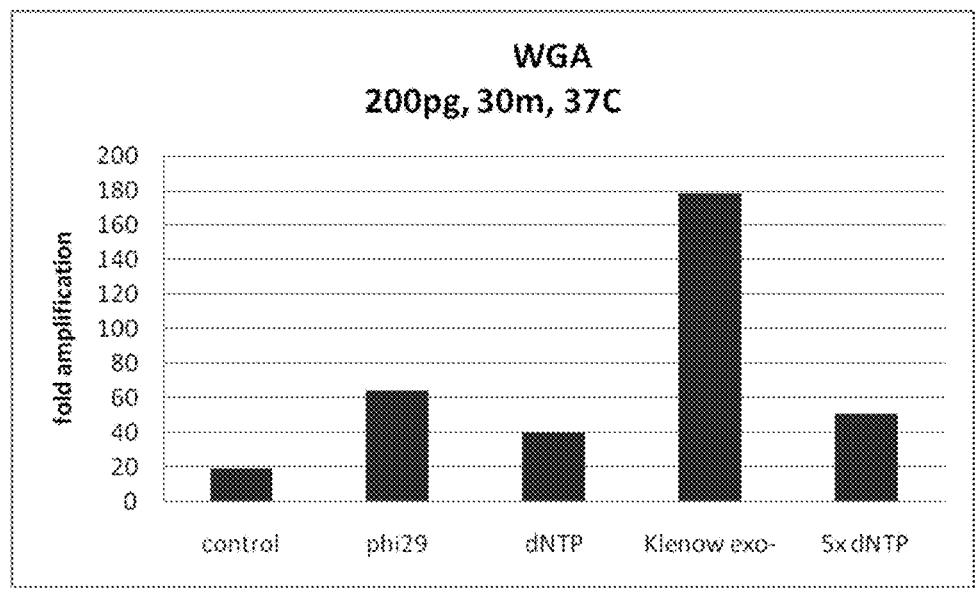
FIG. 5 shows fold-amplification WGA results from Example 5 where various conditions and enzymes were tested in A9 buffer.

All reactions were set up to be in a 100 ul total volume. For each reaction, 70 ul A9 complete was combined with 1 ul (200 pg/ul) K. pneumoniae genomic DNA and 19 ul of $H_2O$. This was heated to 95 C for 2 minutes, and then cooled to 4 C and held at 4 C for 10 m. Reaction 1 is the control reaction, to which was added 5 ul of $H_2O$. Reaction 2 received 4 ul of $H_2O$ and 1 ul of phi29 DNA polymerase (100 u/ul). Reaction 3 received 4 ul of $H_2O$ and 1 ul of dNTP (10 mM each). Reaction 4 received 4 ul of $H_2O$ and 1 ul of E. coli DNA polymerase Klenow fragment exo- (40 u/ul). Reaction 5 received 5 ul of dNTP. To all reactions was added 1 bead of lyophilized enzyme B4. The reactions were mixed well and incubated at 37 C for 30 minutes, followed by 65 C for 10 m and then stored at -20 C overnight. The quantization was done with qPCR specific for K. pneumoniae DNA. The results are shown in FIG. 5.

Example 6

WGA Enhancement with Klenow Exo-

In this Example, all reactions were set up in 100 ul total volume with A9 complete buffer. Each reaction contained 70 ul of A9 buffer, 1 ul of K. pneumoniae DNA (200 pg/ul), and 21 ul of $H_2O$. All reactions were heated to 95 C for 1 m and then held at 4 C for 5 m.

To reaction 2, 6 u of Klenow DNA polymerase.

To reaction 3, 18 u of Klenow.

To reaction 4, 6 u of Klenow exo-.

To reaction 5, 18 u of Klenow exo-.

To reaction 6, 40 u of Klenow exo-.

Figure 6:
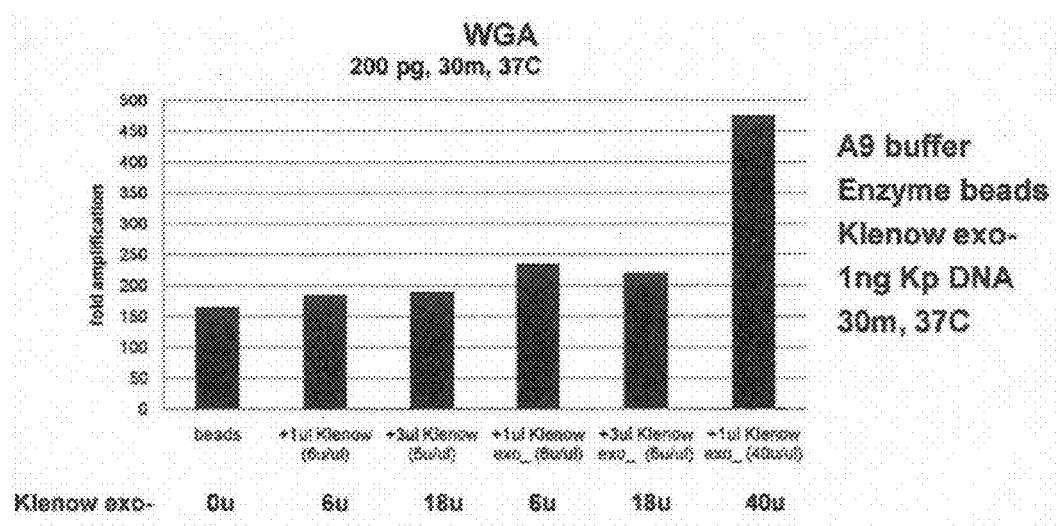
FIG. 6 shows fold-amplification WGA results from Example 6 where various amounts of Klenow exo– were tested in A9 buffer.

All reactions were brought to 95 ul with $H_2O$. To all reactions was added 1 WGA enzyme pellet. The reactions were vortexed and heated at 37 C for 30 minutes, followed by 65 C for 10 m and stored at -20 C. The quantitation was performed with qPCR specific for Kp DNA. The results are shown in FIG. 6, which shows that 40 u of Klenow exo- enhances fast WGA, while Klenow did not in this particular Example.

Example 7

WGA Enzyme Optimization Phi29 Titration+/-Klenow Exo-

In this Example, all reactions were at 100 ul volume in thin walled PCR tubes, with A9 complete buffer and 1 ng of Kp DNA. All reactions were heated to 95 C for 1 m and then held at 4 C for 5 m. Reaction 1 received 25 u of phi29 DNA polymerase, reaction 2 got 50 u, reaction 3 got 100 u, reaction 4 received 25 u, reaction 5 received 50 u and reaction 6 received 100 u of phi29DNA polymerase. In addition, reaction 4-6 received 40 u of Klenow exo-.

Figure 7:
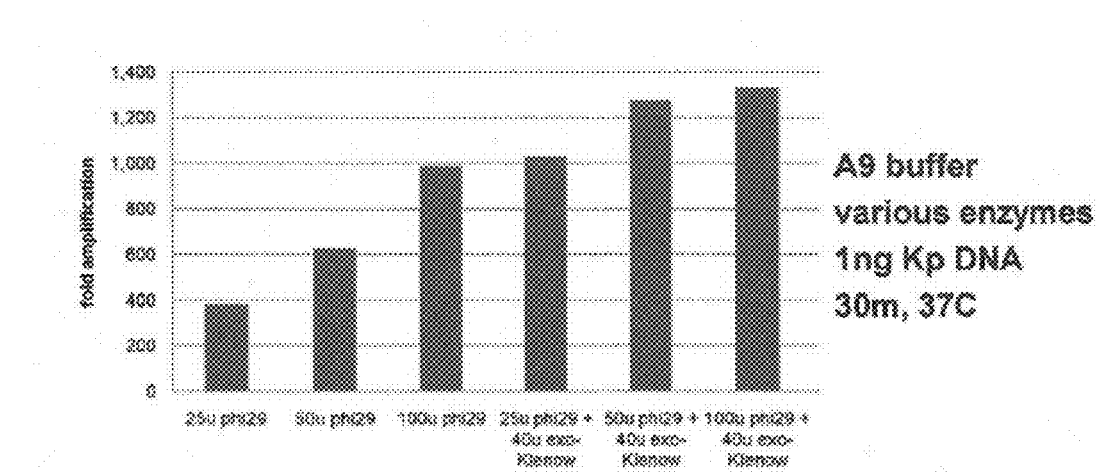
FIG. 7 shows fold-amplification WGA results from Example 7 where various enzymes were tested in A9 buffer.

The reactions were incubated at 37 C for 30 minutes, followed by 75 C for 10 m and then held at 4 C till required. Quantitation was with KP specific qPCR reactions. FIG. 7 shows the results, which shows that 100 u phi29+40 u Klenow exo- works well for fast WGA (giving over 2,500 fold amplification in 30 minutes).

Example 8

WGA dNTP Optimization

Figure 8:
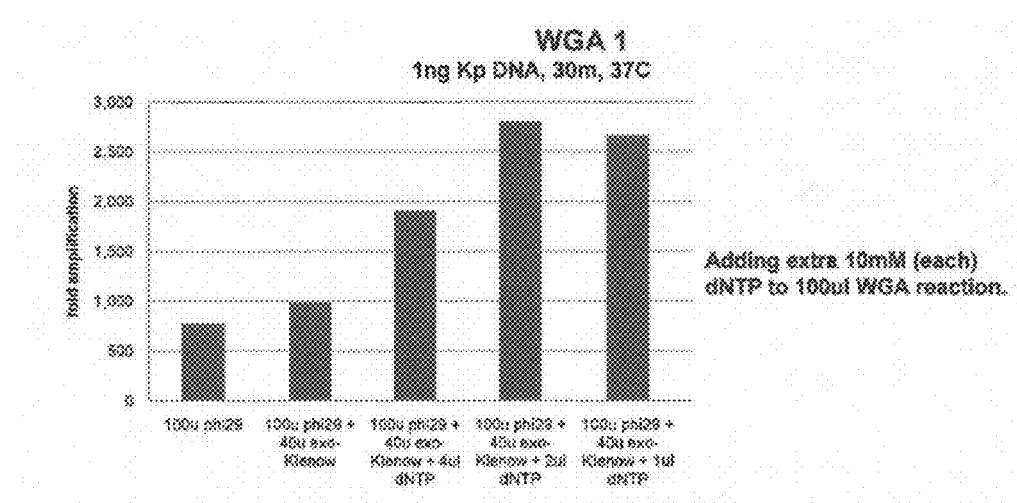
FIG. 8 shows fold-amplification WGA results from Example 8 where various concentrations of dNTPs were tested.

In this Example, each reaction was 100 ul in thin walled PCR tubes with A9 complete buffer with 1 ng of Kp DNA. All reactions were heated to 95 C for 1 minute and then held at 4 C for 5 minutes. Reaction 1-5 received 100 u of phi29 DNA polymerase. In addition, reaction 2-5 received 40 u of Klenow exo- enzyme. Also, reaction 3-5 received additional dNTP. Reaction 3 received a 400 uM increase in dNTP, reaction 4 received a 200 uM increase and reaction 5 received a 100 uM increase. All reactions were vortexed well, and incubated at 37 C for 30 minutes, followed by 75 C for 10 minutes and then held at 4 C. Quantitation was with KP specific qPCR reactions. FIG. 8 shows the results and shows that additional dNTP further enhances the fold amplification for WGA.

Example 9

Exemplary WGA Conditions

Figure 9:
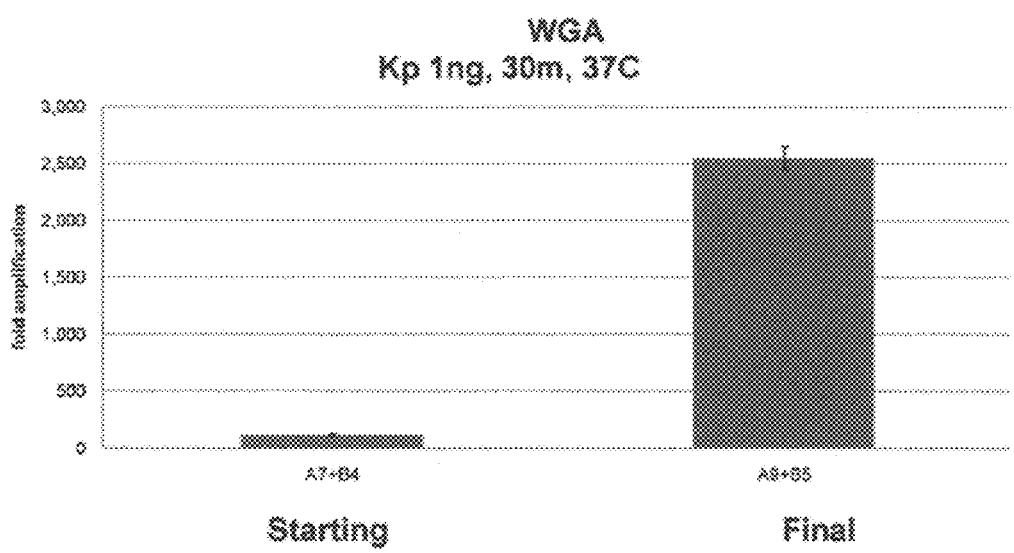
FIG. 9 shows a comparison of the WGA fold-amplification results using the A7 buffer (with B4 enzyme mix) and the A9 buffer (using the B5 enzyme mix) as described in Example 9.

In this Example, all reactions were at 100 ul in thin walled PCR tubes. Reaction 1 contained buffer A7 and the B4 enzyme cocktail. Reaction 2 contained buffer A9 and 100 u of phi29 DNA polymerase and 40 u of Klenow exo- and a 200 uM increase in dNTP. Both reactions used 1 ng of *K. pneumoniae* DNA as starting material. Prior to the enzyme addition, the reactions were heated to 95 C for 1 minute followed by 4 C for 5 minutes. Then the appropriate enzyme cocktails were added and the reactions were mixed well. Reaction 1 was incubated at 30 C for 30 minutes, reaction 2 was incubated at 37 C for 30 minutes. Then both reactions were heated to 75 C for 10 minutes and held at 4 C. Quantitation was with KP specific qPCR reactions. FIG. 9 shows the results that shows that the A9 buffer and B5 enzyme mix (B5 enzyme mix—100 u phi29 DNA pol, 40 u Klenow exo-, 20 mM dNTP) provided dramatically superior results, with over 2500-fold amplification in 30 minutes by WGA.

Example 10

Exemplary Fast WGA Conditions

This Example compares the standard A7 buffer to the A9 buffer of the present invention with additional dNTPs. All reactions were at 100 ul total volume and contained 1 ng of Kp DNA template. All reactions were heated to 95 C for 1 minute and then held at 4 C for 5 minutes prior to enzyme addition. All reaction conditions were tested in triplicate.

Figure 10:
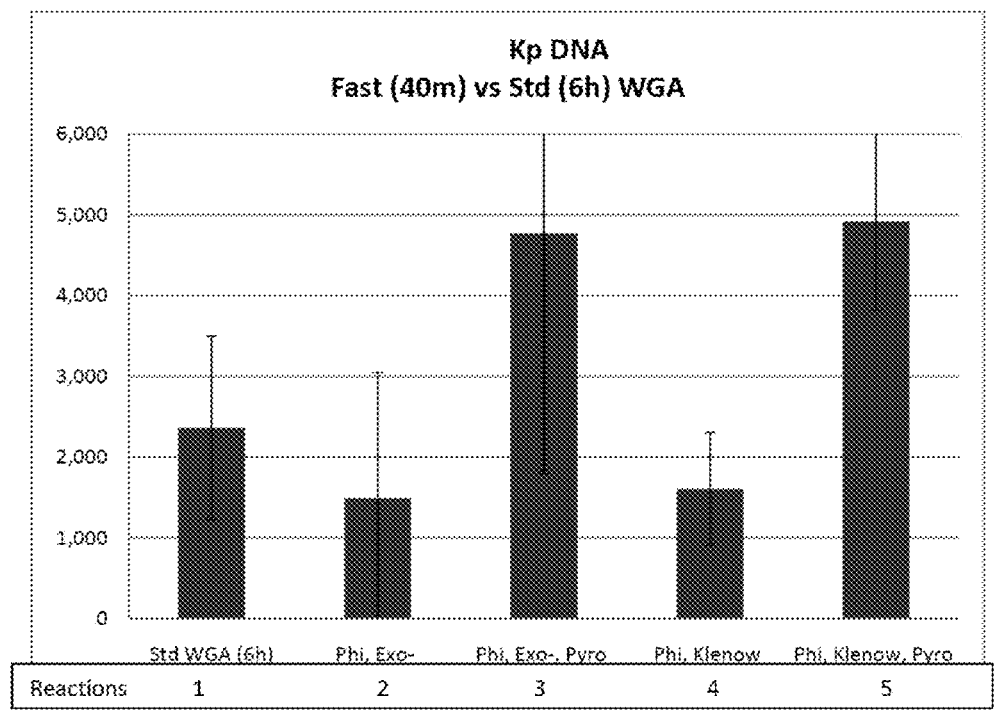
FIG. 10 shows a comparison of the WGA fold-amplification between standard conditions (using 6 hours) and various combinations of Phi29, Klenow or Klenow exo–, and pyrophosphatase (using 40 minutes).

The standard WGA reaction (reaction #1) contained A7 complete buffer and B4 enzyme cocktail. The reaction was for 6 hours at 30 C, followed by 65 C for 10 minutes. Reaction #2 was with A9 buffer, 100 u phi29 DNA polymerase and 40 u of Klenow exo- DNA polymerase. Reaction #3 was identical to reaction #2 with the addition of 0.02 u of pyrophosphatase. Reaction #4 was with A9 buffer, 100 u phi29 DNA polymerase and 50 u of Klenow DNA polymerase. Reaction #5 was identical to reaction #4 with the addition of 0.02 u of pyrophosphatase. Reactions 2-5 were incubated at 37 C for 40 m, then 75 C for 10 m. FIG. 10 shows the results.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

---

We claim:

1. A method of amplifying target nucleic acid comprising:
   a) providing a sample comprising: i) target nucleic acid, ii) phi29 polymerase, iii) exo- Klenow polymerase, iv) dNTPs, v) primers, vi) a buffering agent, and vi) poly(adenylic) acid; and
   b) treating said sample under conditions such that said target nucleic acid is amplified thereby generating amplified target nucleic acid.

2. The method of claim 1, wherein said treating is under isothermal conditions.

3. The method of claim 1, wherein said target nucleic acid is amplified at a rate that would result in at least 500-fold amplification in 30 minutes.

4. The method of claim 1, wherein said target nucleic acid is amplified at a rate that would result in at least 2000-fold amplification in 30 minutes.

5. The method of claim 1, wherein said target nucleic acid is present in said sample at a level between 1 ng and 100 ng.

6. The method of claim 1, wherein said primers are random primers.

7. The method of claim 1, wherein said target nucleic acid is genomic DNA.

8. The method of claim 1, wherein said sample further comprises a phosphatase.

9. The method of claim 1, wherein said sample further comprises a pyrophosphatase.

10. The method of claim 1, wherein said dNTPs are at a concentration of at least 10 mM of each of the four bases.

11. The method of claim 1, wherein said sample further comprises at least one component selected from the group consisting of: an emulsifier, a divalent metal cation, an inorganic salt, an alpha-linked disaccharide, and a reducing agent.

12. The method of claim 1, wherein said buffering agent comprises Tris, $MgCl_2$, $(NH_4)_2SO_4$, Trehalose, and 1% (w/v) nonionic sorbitan ester surfactant.

13. A method for amplifying target nucleic acid comprising:
- a) providing a sample comprising i) a target nucleic acid, ii) phi29 polymerase, iii) exo– Klenow polymerase, iv) pyrophosphatase, v) primers, vi) dNTPs, vii) a buffering agent comprising Tris, MgCl$_2$, (NH$_4$)$_2$SO$_4$, Trehalose, and 1% (w/v) nonionic sorbitan ester surfactant, and viii) a reducing agent
- b) treating said sample under conditions such that said target nucleic acid is amplified thereby generating amplified target nucleic acid.

14. The method of claim 13, wherein said phi29 polymerase is 100 u phi29 polymerase and said exo– Klenow polymerase is 40 u exo– Klenow polymerase.

15. The method of claim 13, wherein said buffering agent comprises Tris pH 7.6, 12 mM MgCl$_2$, 10 mM (NH$_4$)$_2$SO$_4$, 566 mM Trehalose, and 1% (w/v) nonionic sorbitan ester surfactant.

16. The method of claim 13, wherein said dNTPs are at a concentration of at least 10 mM of each of the four bases.

17. The method of claim 16, wherein said dNTPs are 20 mM of each of the four bases.

18. The method of claim 13, wherein said reducing agent is DTT.

* * * * *

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (10)..(15)
<223> OTHER INFORMATION: n is a, c, g, or t

<400> SEQUENCE: 1
cgactcgagn nnnnnatgtg g                                             21
```